United States Patent [19]

Chang

[11] Patent Number: 4,906,281

[45] Date of Patent: Mar. 6, 1990

[54] HERBICIDAL 9-ARYLIMINO-8-THIA-1,6-DIAZABICYCLO [4.3.0]NONANE-7-ONES (AND THIONES)

[75] Inventor: Jun H. Chang, Princeton Junction, N.J.

[73] Assignee: FMC Corporation, Philadelphia, Pa.

[21] Appl. No.: 214,278

[22] Filed: Jul. 1, 1988

[51] Int. Cl.[4] .................... A01N 43/82; C07D 513/04
[52] U.S. Cl. ............................. 71/90; 544/3; 544/224; 544/235; 540/467; 540/544
[58] Field of Search .................. 544/235, 3; 548/138, 548/141; 71/90; 540/467, 544

[56] References Cited

U.S. PATENT DOCUMENTS

| | | | |
|---|---|---|---|
| 4,439,229 | 3/1984 | Swithenbank | 71/96 |
| 4,812,161 | 3/1989 | Hagiwara et al. | 71/90 |
| 4,816,063 | 3/1989 | Yamaguchi et al. | 71/90 |

FOREIGN PATENT DOCUMENTS

| | | |
|---|---|---|
| 0011693 | 6/1980 | European Pat. Off. . |
| 0191303 | 8/1986 | European Pat. Off. . |
| 58-189178 | 11/1983 | Japan . |
| 62-91 | 3/1986 | Japan . |
| WO87/03782 | 7/1987 | PCT Int'l Appl. . |
| WO87/03873 | 7/1987 | PCT Int'l Appl. . |
| 1039442 | 8/1966 | United Kingdom ........ 71/90 |

OTHER PUBLICATIONS

Abstract (Derwent) 87-0407 49/06 for Japan 62-91.
Abstract (Derwent) 41829C/24 of European 0 011 693.
Abstract (Derwent) 83-841268/50 for Japan 189178.

*Primary Examiner*—Mukund J. Shah
*Assistant Examiner*—Emily Bernhardt
*Attorney, Agent, or Firm*—Robert M. Kennedy; Beverly K. Johnson; Abner Sheffer

[57] ABSTRACT

Disclosed are herbicidal compounds of the formula

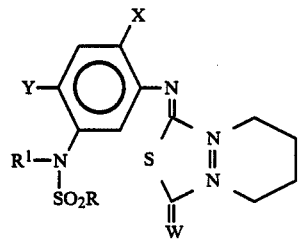

wherein
W is sulfur or oxygen;
X is Br, Cl, F, alkyl, or haloalkyl; Y is Br, Cl, F, methyl, haloalkyl, haloalkoxy, nitro, or a radical of the formula —$CH_2QR^8$ in which Q is O, S, S(O), or $S(O)_2$ and $R^8$ is alkyl, alkenyl, alkynyl, optionally substituted phenyl; R is alkyl, haloalkyl, dialkylamino, carboxymethyl, hydroxy, or optionally substituted phenyl; $R^1$ is hydrogen, alkyl, benzyl, haloalkyl, alkoxy, alkynyl, alkenyl, alkoxymethyl, cyanomethyl, hydroxycarbonylmethyl, alkoxycarbonylmethyl, or a group of the formula —$SO_2R$ or —alkylene—$SO_2R$ in which R is as defined above; or R and $R^1$ together are a divalent alkylene radical; or a base addition salt of a compound as defined above in which R or $R^1$ is or contains an acidic proton.

12 Claims, No Drawings

HERBICIDAL 9-ARYLIMINO-8-THIA-1,6-DIAZABICYCLO[4.3.0]NONANE-7-ONES (AND THIONES)

This invention relates to herbicidal compounds of the general formula

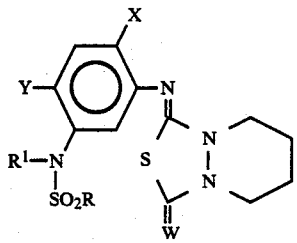

Formula I wherein
- W is sulfur or oxygen;
- X is bromine, chlorine, fluorine, alkyl (e.g., $CH_3$) or haloalkyl (e.g. $CF_3$);
- Y is bromine, chlorine, fluorine, methyl, haloalkyl (e.g. $CH_2F$ or $CF_3$), haloalkoxy (e.g. $OCHF_2$), nitro, a radical of the formula $-CH_2QR^8$ in which Q is O, S, S(O), or $S(O)_2$ and $R^8$ is $C_1-C_3$alkyl, $C_2-C_5$alkenyl, or $C_3-C_5$alkynyl (e.g. $-CH_2OCH_3$, $-CH_2SCH_3$, $-CH_2OCH_2CH=CH_2$, $-CH_2SCH_2CH=CH_2$, $-CH_2OCH_2C\equiv CH$, or $CH_2SCH_2C\equiv CH$); $R^8$ may also be phenyl or phenyl substituted with e.g. halogen, alkyl, haloalkyl;
- R is alkyl (such as straight or branched chain lower alkyl, e.g. methyl, ethyl, propyl), haloalkyl (such as $CF_3$ or $CHF_2$), dialkylamino, carboxymethyl, hydroxy or aryl (such as phenyl, optionally substituted with one or more of: halogen such as Cl, Br or F; alkyl such as lower alkyl, e.g. methyl; alkoxy such as lower alkoxy, e.g. methoxy; cyano; cyanomethyl; nitro; amino; arylamino such as phenylamino; mono- and dialkylamino such as methylamino or dimethylamino; hydroxycarbonyl; alkoxycarbonyl such as $-CO_2C_2H_5$; alkoxyalkyl such as alkoxymethyl of 2 to 4 carbon atoms; alkoxycarbonylalkyl such as $-CH_2CO_2C_2H_5$; benzyl; or hydroxy);
- $R^1$ is hydrogen, alkyl (e.g. straight or branched chain lower alkyl such as methyl, ethyl, propyl, isopropyl or butyl), benzyl, haloalkyl (e.g. $CHF_2$ or $CH_2CH_2CH_2F$), alkoxy (e.g. methoxy), alkynyl (such as propargyl), alkenyl (such as allyl), alkoxymethyl (such as methoxymethyl), cyanomethyl, hydroxycarbonylmethyl (and agriculturally acceptable salts thereof), alkoxycarbonylmethyl (e.g. $-CH_2CO_2CH_3$), a group of the formula $-SO_2R$ or $-$alkylene$-SO_2R$ in which, for example, said alkylene group has 1 to 4 carbon atoms (e.g. $-CH_2-$) and R is as defined above, or
  - R and $R^1$ together may be a divalent radical such as alkylene (e.g. of 3 to 10 carbon atoms such as 1,3-propylene).
- $R^1$ may also be an agriculturally acceptable salt-forming group such as a metal ion (e.g. Na, K or Ca) or ammonium (e.g. $NH_4$ or lower alkyl-substituted ammonium) or sulfonium or sulfoxonium (such as salts of bases of the formula $R''_3S(O)_n$ where $R''$ is, for instance, lower alkyl (e.g. $C_1-C_3$alkyl) and n is zero or one, e.g. the trimethylsulfoxonium salt).

In each aspect of the invention, it is often preferable that any alkyl, alkenyl, alkynyl or alkylene radical have less than 6 carbon atoms.

Representative compounds according to the invention are shown in Table 1 below.

The compounds of this invention may be prepared by the use of steps generally described in the literature or by methods analogous or similar thereto and within the skill of the art. In the Example below an arylamine is treated to form the corresponding aryl isothiocyanate (e.g. by reaction with thiophosgene in the presence of triethylamine). Without the need for separating or purifying the isothiocyanate, the latter was reacted with perhydropyridazine (in its salt form, e.g. its hydroiodide, in the presence of triethylamine and a solvent such as methylene chloride) to form a compound of the formula

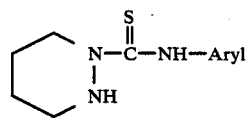

Formula II

The compound of formula II is then reacted with phosgene or thiophosgene (in the presence of pyridine and a solvent such as methylene chloride) to form a compound of the formula:

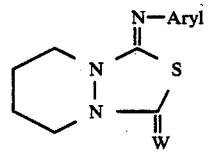

Formula III

In the process in the Example below the aryl radical is initially a 2-fluoro-4-chloro-5-nitrophenyl radical, and the $NO_2$ group is subsequently reduced to form an amino group which is then converted to the desired sulfonamido group. The modification of the aryl moiety of the molecule to introduce the desired X, Y and sulfonamide substituents may be effected at various stages of the process.

This invention is illustrated further in the following Example. In this application, all parts are by weight and all temperatures are in °C. unless otherwise specified.

EXAMPLE 1

9-(4-Chloro-5-ethylsulfonylamino-2-fluorophenyl)imino-8-thia-1,6-diazabicyclo[4.3.0]nonane-7-thione Step A: 4-Chloro-2-fluoro-5-nitrophenylisothiocyanate To a cold (0° C.), stirring mixture of 12.0 g (0.0630 mole) of 4-chloro-2-fluoro-5-nitroaniline in 100 mL of methylene chloride was added dropwise 7.3 g (0.063 mole) of thiophosgene. While maintaining a temperature of 0° C., 13.2 g (0.130 mole) of triethylamine was added dropwise to the mixture. After complete addition, the mixture was allowed to warm to room temperature and stir for approximately 18 hours. The solvent was evaporated under reduced pressure leaving a residue. This residue was stirred in a mixture of ethyl acetate and n-heptane (30:70). The insoluble amine hydrochloride salts were removed by filtration. The filtrate was evaporated under reduced pressure to yield 14.0 g of 4-chloro-2-fluoro-5-nitrophenylisothiocyanate.

The ir and nmr spectra were consistent with the proposed structure.

Step B: Perhydropyridazine hydroiodide

Hydrogenation of 40.0 g (0.175 mole) of 1,2-dicarboethoxy-1,2,3,6-tetrahydropyridazine with 0.33 g of 10% palladium on charcoal in 100 mL of ethanol produced 37.0 g of 1,2-dicarboethoxyperhydropyridazine.

In a manner similar to that described by Jung et al., T.S.C. Chem. Comm. 1978, 315, the reaction of 37.0 g of 1,2-dicarboethoxyperhydropyridazine with 82.0 g (0.410 mole) of iodotrimethylsilane in approximately 250 mL of chloroform followed by the careful addition of methanol produced 20.5 g of perhydropyridazine hydroiodide.

The ir and nmr spectra were consistent with the proposed structure.

Step C: N-(4-chloro-2-fluoro-5-nitrophenylaminothiocarbonyl)perhydropyridazine

To a stirred, cold (−5° C.) solution of 8.56 g (0.0400 mole) of perhydropyridazine hydroiodide in 150 mL of methylene chloride was added dropwise 12.2 g (0.120 mole) of triethylamine. This mixture was stirred for approximately 30 minutes. A solution of 8.0 g (0.034 mole) of 4-chloro-2-fluoro-5-nitrophenylisothiocyanate in methylene chloride was added dropwise to the reaction mixture while maintaining a reaction temperature of −20° C. After complete addition, the reaction mixture was allowed to warm to room temperature and was stirred for two days. The solvent was removed from the mixture by evaporation under reduced pressure leaving a residue. The residue was subjected to column chromatography on silica gel, eluting with ethyl acetate:n-heptane (50:50), to yield 10.4 g of N-[(4-chloro-2-fluoro-5-nitrophenyl)aminothiocarbonyl]perhydropyridazine as a solid, mp 118°–120° C.

The ir and nmr spectra were consistent with the proposed structure.

Step D: 9-(4-Chloro-2-fluoro-5-nitrophenyl)imino-8-thia-1,6-diazabicyclo[4.3.0]nonane-7-thione While maintaining a reaction temperature of −5° C., 7.75 g (0.0850 mole) of pyridine was added dropwise to a stirred solution of 9.0 g (0.028 mole) of N-(4-chloro-2-fluoro-5-nitrophenylaminothiocarbonyl)perhydropyridazine in 250 mL of methylene chloride. To this mixture was added dropwise 3.25 g (0.0282 mole) of thiophosgene. This mixture was stirred at −5° C. for 30 minutes, then was allowed to warm to room temperature and was stirred for approximately 18 hours. The reaction mixture was washed with an aqueous, 5% hydrochloric acid solution followed by an aqueous, saturated sodium chloride solution. The washed reaction mixture was dried over anhydrous magnesium sulfate and was filtered. The filtrate was evaporated under reduced pressure leaving a solid residue. The residue was purified by recrystallization to yield 4.5 g of 9-(4-chloro-2-fluoro-5-nitrophenyl)imino-8-thia-1,6-diazabicyclo[4.3.0]nonane-7-thione, mp 171°–173° C.

The ir and nmr spectra were consistent with the proposed structure.

Step E: 9-(5-Amino-4-chloro-2-fluorophenyl)imino-8-thia-1,6-diazabicyclo[4.3.0]nonane-7-thione To a stirred, hot (75° C.) mixture of 1.4 g (0.025 mole) of iron powder in 200 mL of acetic acid was added 1.5 g (0.0042 mole) of 9-(4-chloro-2-fluoro-5-nitrophenyl)imino-8-thia-1,6-diazabicyclo[4.3.0]nonane-7-thione. The mixture was stirred at 75° C. for one hour, then filtered and the filtrate evaporated under reduced pressure leaving a residue. The residue was partitioned between ethyl acetate and an aqueous, saturated sodium bicarbonate solution. The organic phase was separated, dried over anhydrous magnesium sulfate, and filtered. The filtrate was evaporated under reduced pressure to yield 1.1 g of 9-(5-amino-4-chloro-2-fluorophenyl)imino-8-thia-1,6-diazabicyclo[4.3.0]nonane-7-thione as a solid, mp 59°–61° C.

The ir and nmr spectra were consistent with the proposed structure.

Step F: 9-(4-Chloro-5-ethylsulfonylamino-2-fluorophenyl)imino-8-thia-1,6-diazabicyclo[4.3.0]nonane-7-thione A mixture of 0.45 g (0.0014 mole) of 9-(5-amino-4-chloro-2-fluorophenyl)imino-8-thia-1,6-diazabicyclo[4.3.0]nonane-7-thione, 0.18 g (0.0014 mole) of ethanesulfonyl chloride, and 0.22 g (0.027 mole) of pyridine in approximately 30 mL of methylene chloride was stirred at room temperature for two days. The reaction mixture was heated at 26° C. for approximately 24 hours, then at reflux for 36 hours. The solvent was evaporated from the mixture leaving an oily residue. The residue was washed with an aqueous, 10% hydrochloric acid solution. The washed residue crystallized upon standing and was recrystallized from ethyl acetate and n-heptane to give 0.12 g of 9-(4-chloro-5-ethylsulfonylamino-2-fluorophenyl)imino-8-thia-1,6-diazabicyclo[4.3.0]nonane-7-thione, mp 146°–148° C., Compound 11 of Table 1.

The ir and nmr spectra were consistent with the proposed structure.

The compound of this Example (Step F) gave the following results (expressed as percent control) in tests for herbicidal activity. The testing procedure was as described below.

| Species | Compound 11 Application Rate 0.125 kg/ha | |
| --- | --- | --- |
| | Preemergence | Postemergence |
| Cotton | 80 | 100 |
| Soybean | 0 | 50 |
| Corn | 0 | 60 |
| Rice | 0 | 5 |
| Wheat | 0 | 25 |
| Morningglory | 40 | 100 |
| Wild Mustard | 100 | 100 |
| Velvetleaf | 100 | 100 |
| Barnyardgrass | 0 | 10 |
| Green Foxtail | 0 | 70 |
| Johnsongrass | 0 | 20 |

HERBICIDAL ACTIVITY

The plant test species used in demonstrating the herbicidal activity of compounds of this invention include cotton (*Gossypium hirsutum* var. DPLGI), soybean (*Glycine max* var. Williams), field corn (*Zea mays* var. Pioneer 3732), wheat (*Triticum aestivium* var. Wheaton), rice (*Oryza sativa* var. Labelle), morningglory (*Ipomea lacumosa* or *Ipomea hederacea*), wild mustard (*Brassica kaber*), velvetleaf (*Abutilon theophrasti*), barnyardgrass (*Echinochloa crus-galli*), green foxtail (*Setaria viridis*), and johnsongrass (*Sorghum halepense*).

Preparation of Flats

Preemergence:

Two disposable fiber flats (8 cm × 15 cm × 25 cm) for each rate of application for each candidate herbicide for preemergence testing are filled to an approximate depth of 6.5 cm with steam sterilized sandy loam soil. The soil is leveled and impressed with a template to provide six evenly spaced furrows 13 cm long and 0.5 cm deep in each flat. Seeds of cotton, soybean, corn, rice and wheat are planted in five of the furrows of the first flat (the sixth furrow is left unplanted), and seeds of wild mustard, morningglory, velvetleaf, barnyardgrass, green foxtail, and johnsongrass are planted in the six furrows of the second flat. The template is again employed to firmly press the seeds into place. A topping soil of equal portions of sand and sandy loam soil is placed uniformly on top of each flat to a depth of approximately 0.5 cm. The flats are first watered, then sprayed with a solution of test compound as described below.

Postemergence:

Two flats for each rate of application for each herbicide candidate are also prepared for postemergence application. The postemergence flats are prepared in the same manner as discussed above for the preemergence flats. The prepared flats are watered for 8–11 days, then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24 g/4 flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Rating Percent Control | Description of Main Categories | Crop Description | Weed Description |
|---|---|---|---|
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound 17.9 parts of Palmetto clay, and 1.0 part of sodium lignosulfonate and 0.3 part of sulfonated aliphatic polyester as wetting agents. Other wettable powder formulations are:

| Component: | % by Wt. |
|---|---|
| Active ingredient | 40.00 |
| Sodium lignosulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkylnaphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | % by Wt. |
|---|---|
| Oil Suspension: | |
| Active ingredient | 25.00 |
| Polyoxyethylene sorbitol hexaoleate | 5.00 |
| Highly aliphatic hydrocarbon oil | 70.00 |
| Total | 100.00 |

| -continued | |
|---|---|
| | % by Wt. |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 1 to 250 g/ha, preferably about 4 to 30 g/ha. For field use, where there are losses of herbicide, higher application rates (e.g. four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methyl-propanenitrile (cyanazine); dinitroaniline herbicides such as 2,6-dinitro-N,N-dipropyl-4-(trifluoromethyl)-benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

Representative Compounds

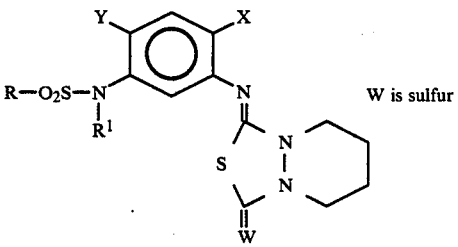

W is sulfur

| Cpd | X | Y | R | R¹ |
|---|---|---|---|---|
| 1 | Cl | Cl | CH₃ | H |
| 2 | F | F | CH₃ | H |
| 3 | F | Cl | CH₃ | H |
| 4 | F | Br | CH₃ | H |
| 5 | F | CH₃ | CH₃ | H |
| 6 | CH₃ | CH₃ | CH₃ | H |
| 9 | Cl | Cl | C₂H₅ | H |
| 10 | F | F | C₂H₅ | H |
| 11 | F | Cl | C₂H₅ | H |
| 12 | CF₃ | Cl | C₂H₅ | H |
| 13 | F | Br | C₂H₅ | H |
| 14 | CH₃ | CH₃ | C₂H₅ | H |
| 16 | Cl | Cl | n-C₃H₇ | H |
| 17 | F | F | n-C₃H₇ | H |
| 18 | F | Cl | n-C₃H₇ | H |
| 19 | F | Br | n-C₃H₇ | H |
| 20 | F | Cl | CH₃ | C₂H₅ |
| 21 | F | Cl | CH₃ | n-C₃H₇ |
| 22 | Cl | Cl | CH₃ | SO₂CH₃ |
| 23 | F | F | CH₃ | SO₂CH₃ |
| 24 | F | Cl | CH₃ | SO₂CH₃ |
| 25 | F | Br | CH₃ | SO₂CH₃ |
| 26 | F | CH₃ | CH₃ | SO₂CH₃ |
| 27 | CH₃ | CH₃ | CH₃ | SO₂CH₃ |
| 28 | F | Cl | CH₃ | SO₂C₂H₅ |
| 29 | F | Cl | C₂H₅ | CH₃ |
| 30 | F | Cl | C₂H₅ | C₂H₅ |
| 31 | F | Cl | C₂H₅ | n-C₃H₇ |
| 32 | F | Cl | C₂H₅ | i-C₃H₇ |
| 33 | F | Cl | C₂H₅ | CH₂OCH₃ |
| 35 | Cl | Cl | C₂H₅ | SO₂C₂H₅ |
| 37 | F | F | C₂H₅ | SO₂C₂H₅ |
| 38 | F | Cl | C₂H₅ | SO₂C₂H₅ |
| 39 | F | Br | C₂H₅ | SO₂C₂H₅ |
| 40 | F | CH₂F | C₂H₅ | SO₂C₂H₅ |
| 41 | CH₃ | CH₃ | C₂H₅ | SO₂C₂H₅ |
| 43 | Cl | Cl | n-C₃H₇ | SO₂C₃H₇(n) |
| 44 | F | F | n-C₃H₇ | SO₂C₃H₇(n) |
| 45 | F | Cl | n-C₃H₇ | SO₂C₃H₇(n) |
| 46 | F | Br | n-C₃H₇ | SO₂C₃H₇(n) |
| 47 | F | Cl | CH₃ | CH₃ |
| 48 | F | Cl | CF₃ | H |
| 49 | F | Cl | CH₃ | n-C₄H₉ |
| 50 | Cl | Cl | CH₃ | C₂H₅ |
| 51 | Cl | Cl | CH₃ | C₃H₇ |
| 52 | Cl | Cl | CH₃ | n-C₄H₉ |
| 53 | F | Cl | C₆H₅ | H |
| 54 | F | Cl | N(CH₃)₂ | H |
| 55 | F | Cl | N(C₂H₅)₂ | H |
| 56 | F | Cl | OH | H |
| 57 | F | Cl | CH₃ | CHF₂ |
| 58 | Cl | F | CH₃ | SO₂CH₃ |
| 59 | Cl | F | C₂H₅ | SO₂C₂H₅ |
| 60 | Cl | F | CH₃ | H |
| 61 | Cl | F | C₂H₅ | H |
| 62 | CH₃ | Cl | CH₃ | SO₂CH₃ |
| 63 | CH₃ | Cl | CH₃ | H |
| 64 | F | NO₂ | CH₃ | SO₂CH₃ |
| 65 | F | NO₂ | CH₃ | H |

TABLE 1-continued

Representative Compounds

[Structure: benzene ring with Y and X substituents, R-O2S-N(R¹)- group, and fused thiadiazine ring system; W is sulfur]

| Cpd | X | Y | R | R¹ |
|-----|---|---|---|-----|
| 66 | F | OCHF₂ | CH₃ | SO₂CH₃ |
| 67 | F | OCHF₂ | CH₃ | H |
| 68 | F | CF₃ | CH₃ | SO₂CH₃ |
| 69 | F | CF₃ | CH₃ | H |
| 70 | F | Cl | —(CH₂)₃— | |
| 71 | F | Cl | —(CH₂)₄— | |
| 72 | F | Cl | —(CH₂)₅— | |
| 73 | F | Cl | —(CH₂)₆— | |
| 74 | F | Cl | CH₂CO₂H | H |
| 75 | F | Cl | CH₃ | OCH₃ |
| 76 | F | Cl | CH₃ | CH₂CH₂CH₂F |
| 85 | F | Cl | C₆H₄Cl(4) | H |
| 86 | F | Cl | C₆H₄CH₃(4) | H |
| 87 | F | Cl | C₆H₄OCH₃(4) | H |
| 88 | Br | Cl | CH₃ | H |
| 89 | Br | Br | CH₃ | H |
| 90 | Br | CF₃ | CH₃ | H |
| 91 | F | Cl | CH₃ | CH₂CO₂H |
| 92 | F | Cl | C₂H₅ | CH₂CO₂H |
| 93 | F | Cl | CH₃ | CH₂CO₂Na |

Other representative compounds are those which are identical with Compounds 1, 2, 5–10, 12, 14–17, 20–23, 26–37, 40–44, 47–87, and 90–93 respectively, except that Y is Br. Still other representative compounds are those which are identical with Compounds 1–67, 70–89, and 91–93 respectively, except that Y is CF₃. Other representative compounds are those that are identical to Compounds 1–87 and 91–93 respectively, except that X is Br. Other representative compounds are those which are identical with Compounds 1–19, 48, 53–55, 60, 61, 63, 65, 67, 69, and 85–90 respectively, except that R¹ is Na (or other salt-forming group). Still others are identical with Compounds 1–93 except that W is oxygen.

I claim:

1. An herbicidal compound of the formula

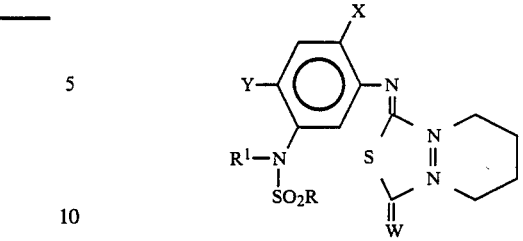

wherein
W is sulfur or oxygen;
X is bromine, chlorine, fluorine, alkyl, or haloalkyl;
Y is bromine, chlorine, fluorine, methyl, haloalkyl, haloalkoxy, nitro, or a radical of the formula —CH₂QR⁸ in which Q is O, S, S(O), or S(O)₂ and R⁸ is C₁-C₃alkyl, C₂-C₅alkenyl, C₃-C₅alkynyl, phenyl, or phenyl substituted with halogen, alkyl, or haloalkyl;
R is alkyl, haloalkyl, dialkylamino, carboxymethyl, hydroxy, phenyl, or phenyl substituted with halogen, alkyl, alkoxy, cyano, cyanomethyl, nitro, amino, phenylamino, mono- and dialkylamino, hydroxycarbonyl, alkoxycarbonyl, alkoxyalkyl, alkoxycarbonylalkyl, benzyl, or hydroxy;
R¹ is hydrogen, alkyl, benzyl, haloalkyl, alkoxy, alkynyl, alkenyl, alkoxymethyl, cyanomethyl, hydroxycarbonylmethyl, alkoxycarbonylmethyl or a group of the formula —SO₂R or —alkylene—SO₂R in which said alkylene has 1 to 4 carbon atoms and R is as defined above; or
R and R¹ together are a divalent alkylene radical of 3 to 10 carbon atoms; or
an agriculturally acceptable base addition salt of a compound as defined above in which R or R¹ is or contains an acidic proton; and wherein any alkyl, alkenyl, alkynyl or alkylene radical has less than 6 carbon atoms.

2. The herbicidal compound of claim 1 in which W is sulfur and each of X and Y is independently selected from fluorine, chlorine, and bromine.

3. The herbicidal compound of claim 2 in which X is fluorine or chlorine and Y is chlorine or bromine.

4. The herbicidal compound of claim 3 in which X is fluorine and Y is chlorine.

5. The herbicidal compound of claim 1 in which W is sulfur and R¹ is hydrogen.

6. The herbicidal compound of claim 1 in which W is sulfur and R is lower alkyl.

7. The herbicidal compound of claim 2 in which R¹ is hydrogen.

8. The herbicidal compound of claim 7 in which R is lower alkyl.

9. The herbicidal compound of claim 8 in which X is fluorine or chlorine and Y is chlorine or bromine.

10. The herbicidal compound of claim 9 in which X is fluorine and Y is chlorine.

11. An herbicidal composition comprising an herbicidally effective amount of a compound of claim 1 in admixture with an agriculturally acceptable carrier.

12. A method for controlling undesired plant growth which comprises applying to the locus where control is desired an herbicidally effective amount of the composition of claim 11.

* * * * *